US012042335B2

(12) United States Patent
Liao et al.

(10) Patent No.: US 12,042,335 B2
(45) Date of Patent: Jul. 23, 2024

(54) SYSTEM AND METHOD FOR BREAST CANCER DETECTION USING CO-LOCALIZED ULTRASOUND-MAMMOGRAPHY

(71) Applicant: Thomas Jefferson University, Philadelphia, PA (US)

(72) Inventors: Lydia C. Liao, Philadelphia, PA (US); Yan Yu, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 46 days.

(21) Appl. No.: 17/637,681

(22) PCT Filed: Aug. 24, 2020

(86) PCT No.: PCT/US2020/047594
§ 371 (c)(1),
(2) Date: Feb. 23, 2022

(87) PCT Pub. No.: WO2021/041295
PCT Pub. Date: Mar. 4, 2021

(65) Prior Publication Data
US 2022/0287687 A1 Sep. 15, 2022

Related U.S. Application Data

(60) Provisional application No. 62/890,819, filed on Aug. 23, 2019.

(51) Int. Cl.
*A61B 8/08* (2006.01)
*A61B 6/00* (2006.01)
*A61B 6/50* (2024.01)

(52) U.S. Cl.
CPC .......... *A61B 8/5261* (2013.01); *A61B 6/4417* (2013.01); *A61B 6/502* (2013.01);
(Continued)

(58) Field of Classification Search
None
See application file for complete search history.

(56) References Cited

U.S. PATENT DOCUMENTS 5,640,956 A * 6/1997 Getzinger .............. A61B 6/502
600/437
6,574,499 B1 * 6/2003 Dines ................... A61B 8/0825
128/915
(Continued)

FOREIGN PATENT DOCUMENTS

DE 199 01 724 * 7/2000
DE 199 01 730 * 7/2000
WO WO 00109014 * 2/2000

OTHER PUBLICATIONS

English translation of DE 199 01 724 (Year: 2000).*
English translation of WO 00/09014 (Year: 2000).*
English translation of DE 199 01 730 (Year: 2000).*

*Primary Examiner* — Katherine L Fernandez
(74) *Attorney, Agent, or Firm* — Riverside Law LLP

(57) ABSTRACT

A system for breast cancer detection using co-localized ultrasound-mammography is disclosed. The system includes an examination box having a cavity connected to a side opening. A compression plate is connected to an actuator, the actuator configured to advance a surface of the compression plate towards a breast positioned within the cavity from the side opening to compress and stabilize the breast. An x-ray device is configured to generate at least one mammography image. An ultrasound probe is configured to generate at least one ultrasound image. A controller is operably connected to the x-ray device and ultrasound probe, the controller configured generate an image based on co-localization of the at least one mammography image and at the least one ultrasound image. A method of performing breast cancer detection and methods of breast imaging are also disclosed.

19 Claims, 14 Drawing Sheets

(52) U.S. Cl.
CPC .......... *A61B 6/5247* (2013.01); *A61B 8/0825* (2013.01); *A61B 8/483* (2013.01)

(56) References Cited

U.S. PATENT DOCUMENTS

| | | | | |
|---|---|---|---|---|
| 7,336,767 | B1* | 2/2008 | Le | G21K 1/025 378/154 |
| 8,747,317 | B2* | 6/2014 | Yu | A61B 8/0825 600/443 |
| 2011/0105900 | A1* | 5/2011 | Entrekin | A61B 8/4455 600/443 |
| 2015/0282770 | A1* | 10/2015 | Klanian | A61B 6/0414 378/208 |
| 2016/0089110 | A1* | 3/2016 | Milkowski | A61B 8/4281 600/472 |
| 2018/0035963 | A1* | 2/2018 | Smith | A61B 6/4441 |
| 2019/0090828 | A1* | 3/2019 | Dederichs | A61B 8/4416 |

\* cited by examiner

SYSTEM AND METHOD FOR BREAST CANCER DETECTION USING CO-LOCALIZED ULTRASOUND-MAMMOGRAPHY

CROSS-REFERENCE TO RELATED APPLICATIONS

This application is a U.S. national stage filing of International application No. PCT/US20/47594 filed on Aug. 24, 2020, which claims priority to U.S. provisional application No. 62/890,819 filed on Aug. 23, 2019, both of which are incorporated herein by reference in their entireties.

BACKGROUND OF THE INVENTION

Breast cancer is the most common cancer in women worldwide, contributing 25.4% of the total number of new cancers diagnosed in 2018. Mammography is used widely in affluent countries in population screening programs, which have been successful in reducing breast cancer mortality rates due to early detection. However, mammography is suboptimal for cancer detection in dense breasts. In the U.S., the "Are You Dense" movement has raised an increased awareness for technology improvements beyond conventional mammography.

Breast MRI is expensive, not widely available, and has some major contraindications. Ultrasound is a complementary imaging modality that can overcome the breast density challenge. However, ultrasound is typically acquired by sonographers performing manual scanning, and recording significant findings for radiologists to perform further interpretation. This process introduces subjectivity and inter-observer variation in conventional ultrasound imaging, which can significantly degrade its diagnostic accuracy. Although technology exists to perform automatic whole breast ultrasound scanning, the resulting ultrasound image set is very large, potentially causing reader fatigue and degradation in sensitivity and/or specificity. A computer-aided lesion classification method does not exist for this automatic whole breast ultrasound technology. For these reasons, the technology is limited. Adding ultrasound to mammogram creates a separate exam and requires extra time, and because of insurance and billing issues, often means a separate appointment for the patient. These logistical challenges also contribute to increased cost for combined mammography and breast ultrasound cancer detection.

Most importantly, there is currently no method to locate a suspicious lesion precisely from one imaging modality to the other between mammography and ultrasound. Comparing the two techniques, the patient is imaged in different positions, in different directions, and at different times between mammogram and ultrasound. Further, a mammogram involves compressing the breast, whereas ultrasound typically does not. Since the two imaging modalities are not co-localized and are acquired with intra-imaging motion, the registration of imaging findings and lesion features is not considered accurate, especially when machine learning, artificial intelligence or similar computer-aided classification algorithms are applied to such mammograms and ultrasound images that are not well registered. These methods are more likely to encounter greater difficulties and generate false predictions.

In low-income and middle-income countries, breast cancer screening by mammography is either non-existent or access to screening unorganized. The level of reader expertise for interpreting mammography can be highly variable. Ultrasound is sometimes used as a low-cost imaging tool. However, the quality of expert interpretation of imaging findings is questionable. In order to improve the diagnostic accuracy of breast cancer when it is still in curable stages, a co-localized ultrasound-mammography system with a simple clinical workflow in a single setting and with automated lesion identification and cancer discrimination capabilities will be highly desirable.

Thus, what is needed in the art is a combined mammography (including 3D digital breast tomography) and 3D ultrasound imaging that can provide an improved patient experience and generate more useful imaging results. Additionally, there is a need to use well-trained machine learning algorithms to assist human interpreters to identify suspicious findings such as cancer features in the combined mammogram-ultrasound image sets. Artificial intelligence is most powerful when a wealth of diverse imaging information of the same object is available and highly correlated. By utilizing co-localization to generate precisely co-registered 3D ultrasound to mammography, computer-aided detection will be able to achieve performance that is considered reliable and useful by expert radiologists.

SUMMARY OF THE INVENTION

In one embodiment, a system for breast cancer detection using co-localized ultrasound-mammography includes an examination box comprising a cavity connected to a side opening, a compression plate connected to an actuator, the actuator configured to advance a surface of the compression plate towards a breast positioned within the cavity from the side opening to compress and stabilize the breast, an x-ray device configured to generate at least one mammography image, an ultrasound probe configured to generate at least one ultrasound image, a controller operably connected to the x-ray device and ultrasound probe, the controller configured to generate an image based on co-localization of the at least one mammography image and at the least one ultrasound image. In one embodiment, the system includes a fluid box in fluid communication with the examination box via a conduit. In one embodiment, the system includes a slidable volume adjustment tray configured into an opening of the fluid box. In one embodiment, the compression plate comprises an interior recess configured to dock the ultrasound probe without an air gap. In one embodiment, the side opening comprises a resilient sealing material configured around at least a portion of a perimeter of the side opening. In one embodiment, the actuator is a mechanical arm. In one embodiment, the ultrasound probe further comprises a probe head disposed within a housing. In one embodiment, the probe head is connected to a dual rail system comprising a first axis rail connected perpendicularly to a second axis rail. In one embodiment, the probe head is connected to at least one of the first axis rail and the second axis rail by a rotatable connector. In one embodiment, the compression plate is positioned above the examination box and the actuator is configured to advance the compression plate downwards into the cavity for compressing and stabilizing a breast during examination. In one embodiment, the compression plate is positioned below the examination box and the actuator is configured to advance the compression plate upwards into the cavity for compressing and stabilizing a breast during examination. In one embodiment, the fluid box is positioned below the examination box. In one embodiment, the ultrasound probe is positioned above the examination box. In one embodiment, the x-ray device is positioned above the ultrasound probe. In one embodiment, the system includes a baffle positioned adjacent to the x-ray device. In one embodiment, the compression plate comprises a low x-ray attenuation material. In one embodiment, the system includes a low x-ray attenuation coupling gel pad for placement within the cavity during an examination. In one embodiment, the ultrasound probe is configured to generate the at least one ultrasound image at a frequency ranging 10 Mhz-30 Mhz. In one embodiment, wherein the x-ray device is configured to generate at least one 3D tomographic mammography image, the ultrasound probe configured to generate at least one 3D ultrasound image, and the controller is configured to generate an image based on co-localization of the at least one 3D tomographic mammography image and at the least one 3D ultrasound image In one embodiment, a method of performing a breast cancer detection procedure includes the steps of compressing and stabilizing a breast using a compression plate, acquiring a mammographic image of the breast, docking an ultrasonic probe onto the compression plate, and acquiring an ultrasonic image of the breast. In one embodiment, the method includes the step of co-localizing the mammographic image and the ultrasonic image. In one embodiment, the method includes the step of acquiring ultrasonic images while the ultrasound probe is scanned in one direction along the compressed breast. In one embodiment, the method includes the step of acquiring ultrasonic images while the ultrasound probe is scanned in two directions along the compressed breast or rotationally around the compressed breast. In one embodiment, the method includes the step of acquiring ultrasonic images while the ultrasound probe is rotated around an axis. In one embodiment, the method includes the step of mathematically compounding images from scanning in the two different directions. In one embodiment, the method includes the step of mathematically compounding images from scanning in at least one linear direction with that from scanning by rotation around an axis. In one embodiment, the method includes the step of padding narrow portions of the breast using a low X-ray attenuating acoustic contact material. In one embodiment, the method includes the step of reducing ultrasonic images to a planar image by raytracing along the mammographic X-ray direction and applying at least one image processing filter to the ultrasound image pixels. In one embodiment, the method includes the step of simulating mammographic x-ray attenuation and transmission through the ultrasound images of the breast. In one embodiment, the method includes the step of identifying one region of interest based on the ultrasound image and displaying the region of interest in the x-ray image. In one embodiment, the method includes the step of identifying one region of interest based on the x-ray image and displaying the region of interest in the ultrasound image. In one embodiment, the method includes the step of filling an air gap surrounding the breast after the step of acquiring a mammographic image of the breast and before the step of acquiring an ultrasonic image of the breast. In one embodiment, the method includes the steps of generating at least one 3D tomographic mammography image, generating at least one 3D ultrasound image, and generating an image based on co-localization of the at least one 3D tomographic mammography image and at the least one 3D ultrasound image.

In one embodiment, a method of breast imaging includes the steps of compressing a breast, measuring a first force exerted in compressing the breast during a first imaging step, compressing the breast at a later time, measuring a second force exerted in compressing the breast during a second imaging step, and comparing the first and second force to determine measurement reliability. In one embodiment, the method includes the step of reproducing the compression force in successive imaging sessions. In one embodiment, the method includes the step of comparing images from successive sessions by mathematical image processing comprising at least one of co-registration, histogram equalization and subtraction.

In one embodiment, a method of breast imaging includes the steps of stabilizing a breast without compression or with partial compression, rotating an X-ray source about a suitable range of angles and acquiring projection images at the angles, and performing tomographic reconstruction to obtain a 3D digital breast tomography image set in the absence of rigorous breast compression In one embodiment, a method of breast imaging includes the steps of acquiring X-ray mammography or digital breast tomography of a breast from only one view, and at least partially compressing the breast in only in one direction. In one embodiment, the X-ray mammography or digital breast tomography is co-registered with 3D ultrasound constructed in the one view.

In one embodiment, a system for breast imaging including an x-ray device configured to generate at least one mammography image, and a concavely shaped X-ray imaging screen and supporting table configured to accommodate the patient's habitus and capture all breast tissues in the image field for generating the at least one mammography image.

In one embodiment, a system for breast imaging includes an x-ray device configured to generate at least one mammography image, and a multi-leaf collimator configured to shape the X-ray field when a patient's habitus is otherwise exposed in the field for generating the at least one mammography image.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

Figure 1A:
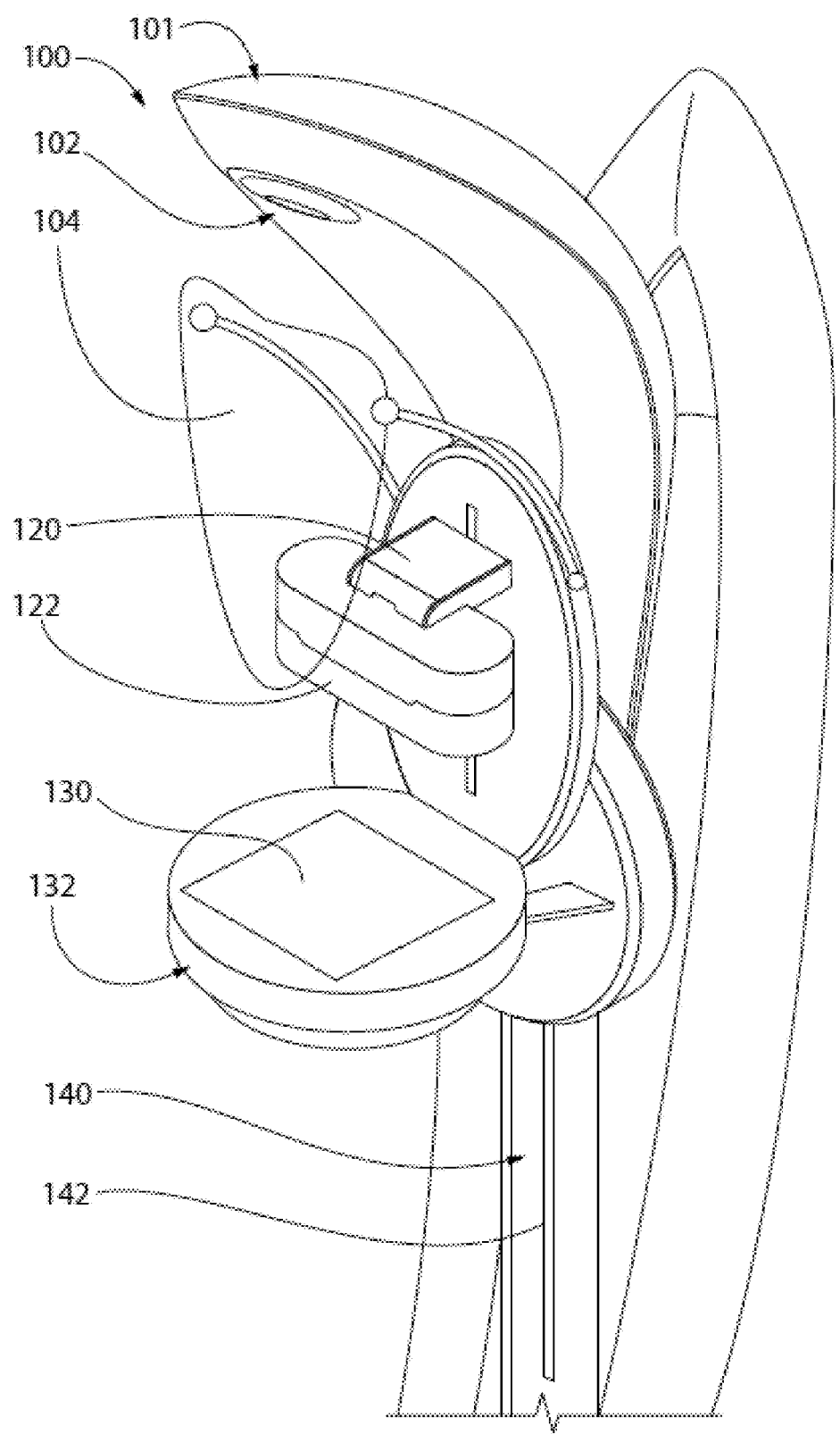
FIGS. 1A-1C are alternate perspective views of a system for breast cancer detection using co-localized ultrasound-mammography according to one embodiment.

It is to be understood that the figures and descriptions of the present invention have been simplified to illustrate elements that are relevant for a more clear comprehension of the present invention, while eliminating, for the purpose of clarity, many other elements found in systems and methods for breast cancer detection using co-localized ultrasound-mammography. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein are systems and methods for breast cancer detection using co-localized ultrasound-mammography.

Traditionally, X-ray imaging of a breast such as planar mammography or 3D digital breast tomography involves breast compression in two directions and acquiring X-ray images in both of these directions. Commonly used directions are medial-lateral oblique (MLO) direction and cranial-caudal (CC) direction. Each breast is irradiated by ionizing radiation two times in order to obtain what is traditionally considered a complete study. Embodiments described herein implement combined mammography (including 3D digital breast tomography) and 3D ultrasound that are co-registered by virtue of co-localized imaging apparatus. Advantageously, only one X-ray imaging direction and thus one 3D digital breast tomography image set is needed. Further, the radiation exposure burden of a patient's breasts is therefore reduced by half. The probability of inducing secondary cancer due to radiation exposure is correspondingly reduced. Still further, the workload of interpreting X-ray images by radiologist is reduced. Embodiments described herein include a system of co-registered multimodality imaging for detecting and characterizing breast diseases such as cancer includes a mammography subsystem and an automated scanning ultrasound subsystem, which are co-localized on a compressed breast. Mammogram and three-dimensional (3D) ultrasound of the compressed breast are acquired in rapid succession without movement of the breast or change in the study subject's position. The resulting co-registered ultrasound and mammography images are interpreted by expert observers, and by computer-based disease classification algorithms.

Embodiments described herein provide several advantages to conventional systems and methods known in the art. For example, mammography is typically performed with the breast compressed between a digital imaging panel and a compression plate, whereas ultrasound scanning subsystems cannot interfere with the X-ray path between the target and the imaging panel. In embodiments of the present invention, solutions for maintaining the same breast compression while switching from mammogram to ultrasound scanning are provided. In one embodiment, the ultrasound scanner enclosure is shaped to fit onto the compression plate precisely and without air gap. A scanning mechanism moves the ultrasound probe inside this enclosure to complete 3D image acquisition. In another embodiment, the mammography imaging panel is not in direct contact with the breast, but rather is situated behind a low X-ray attenuation backplate that serves as compression plate. After the mammogram is acquired, the imaging panel is moved out of the field and the ultrasound scanner is moved in to attach onto the backplate without an air gap.

Another advantage of embodiments described herein addresses the fact that although X-ray mammography is not deleteriously affected by air gaps around the nipple region, ultrasound will suffer from missing signals, causing incomplete scan of the breast tissue. Embodiments of the present invention overcome this challenge by introducing a low X-ray attenuation nipple coupling gel pad between the compression plate that matches to the ultrasound probe and the breast tissue. The coupling gel pad is left in place for both mammogram and ultrasound scans. In another embodiment, ultrasound-coupling fluid is introduced into the examination compartment after X-ray imaging and prior to ultrasound imaging via a reservoir and conduit without disturbing a breast position.

Figure 1B:
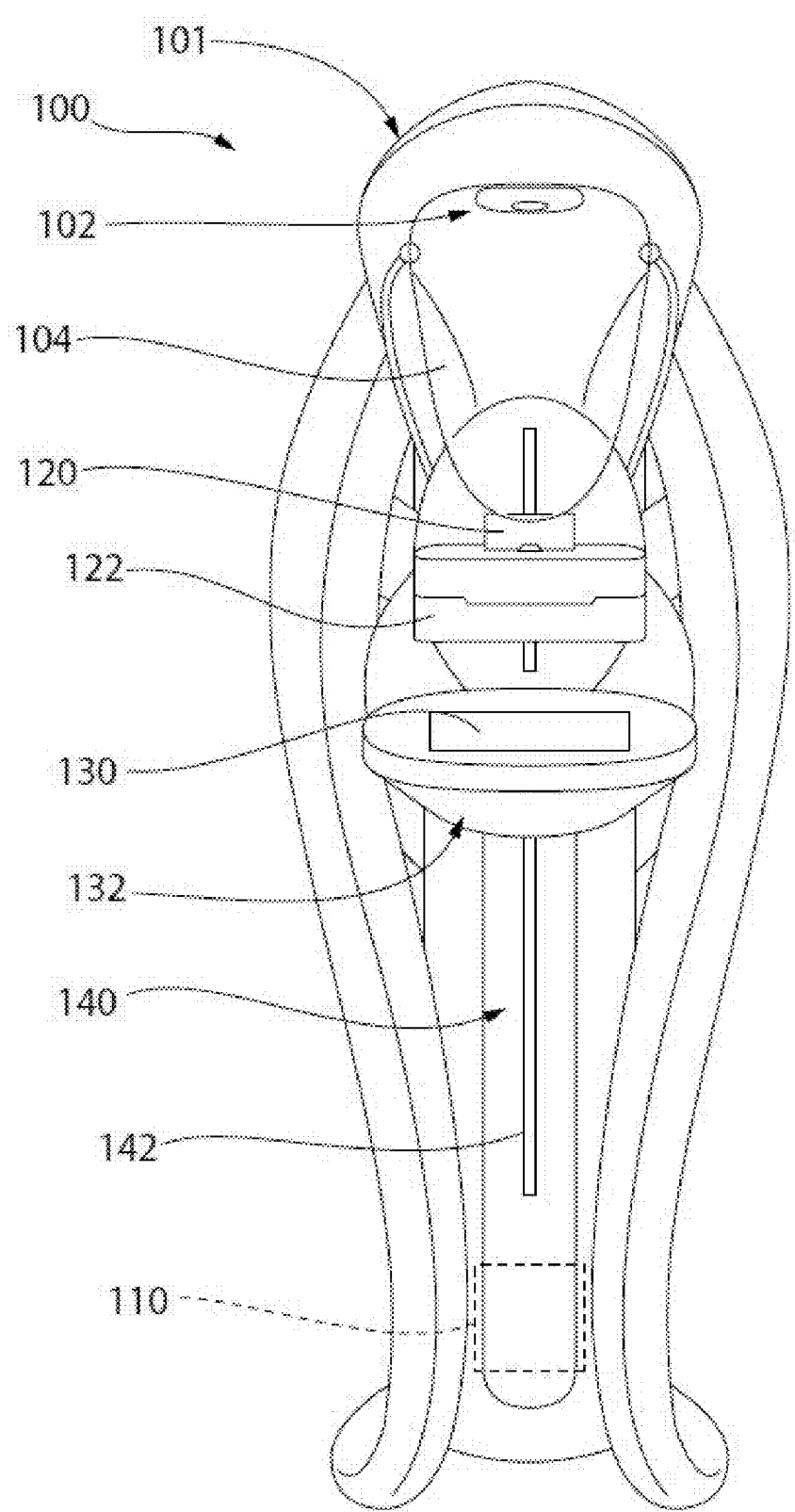
Figure 1C:
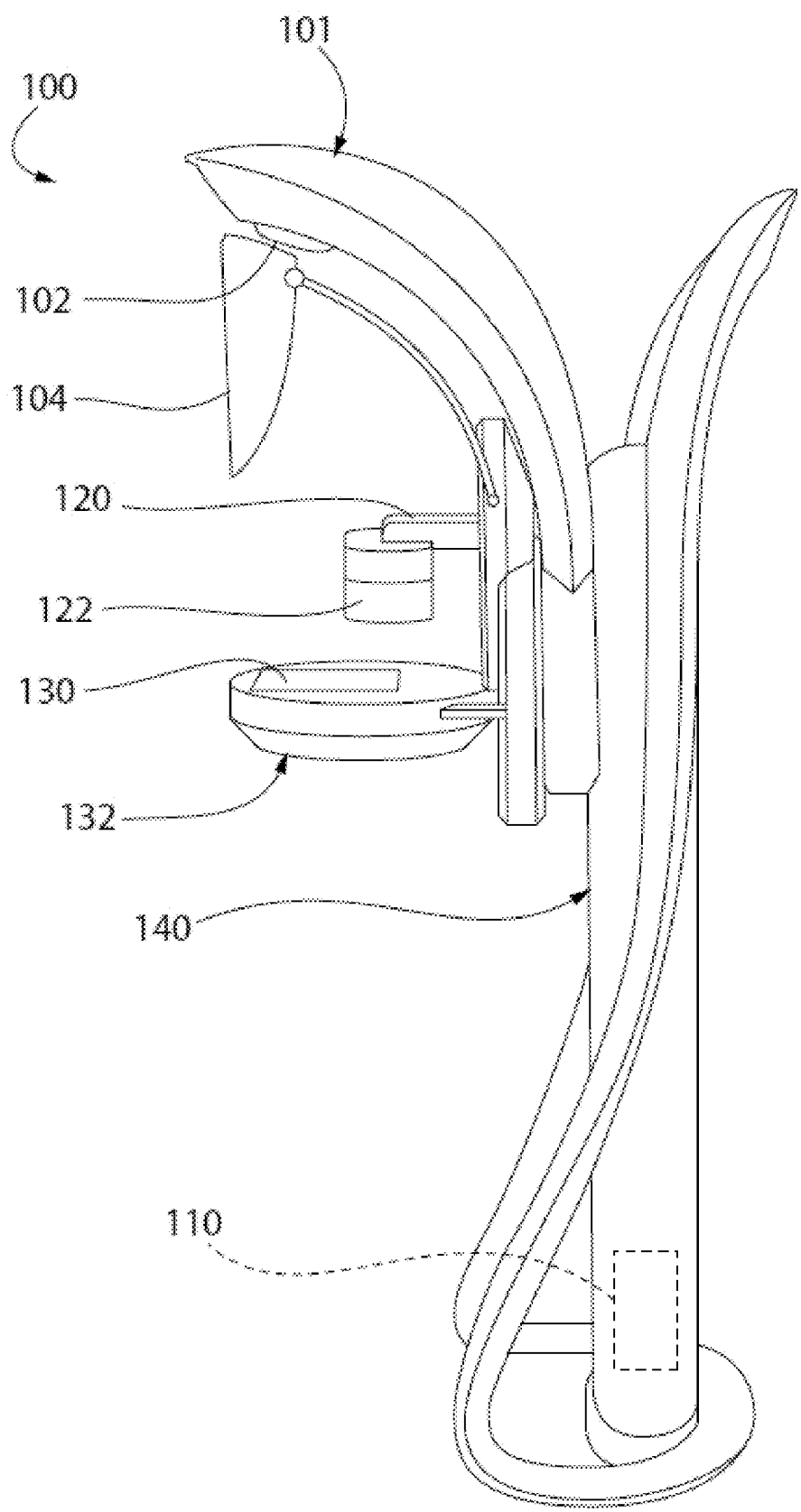

With reference now to FIGS. 1A-1C, a system 100 for breast cancer detection is shown according to one embodiment. The system 100 includes an adjustable housing 101 connected to a cabinet 140. The adjustable housing 101 includes an x-ray device 102 positioned at least partially behind a baffle 104. Configured below the x-ray device 102 and baffle 104 is a 3D ultrasound probe 122 connected to a moving arm 120. Configured below the 3D ultrasound probe 122 is a screen 130 on the top surface of a table 132. The screen 130 can be a standard digital mammography X-ray detector panel, optionally mounted on a supporting platform. The adjustable housing 101 can be raised or lowered by the elevation track 142 configured into the cabinet 140. The adjustable housing 101 can be rotated by a range of angles to achieve 3D tomographic reconstruction. Mammographic X-ray imaging can include 3D tomographic imaging, which according to embodiments described herein can be combined with 3D ultrasound in a co-localized design. This advantageously allows the system to acquire and combine two sets of 3D images of different modalities, co-registered by default via co-localization. The system components are communicatively coupled to a controller 110 or set of controllers, such as through an electrical or wireless connection.

Figure 2A:
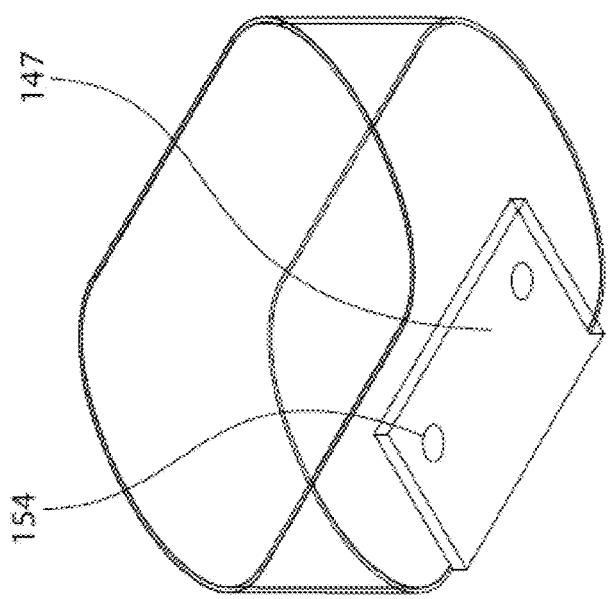
FIG. 2A is a perspective view of a breast examination housing assembly according to one embodiment.
Figure 2A:
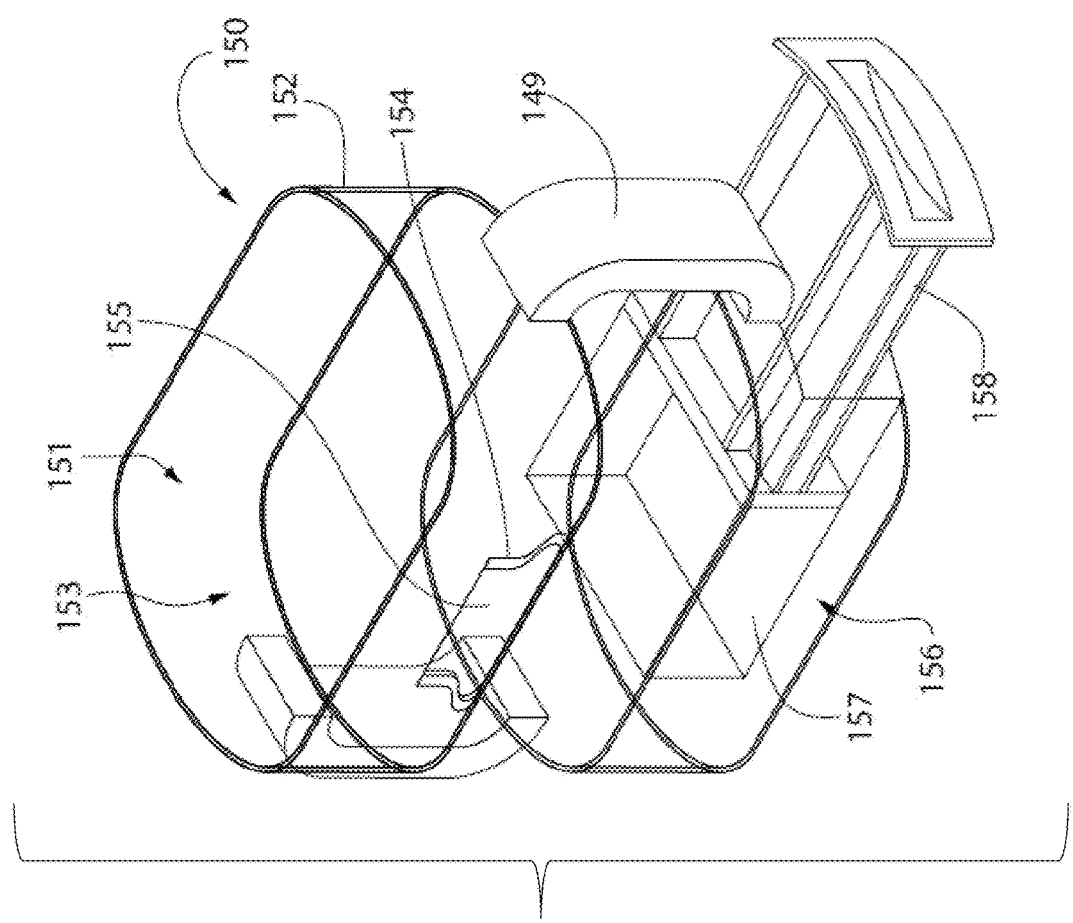
Figure 2B:
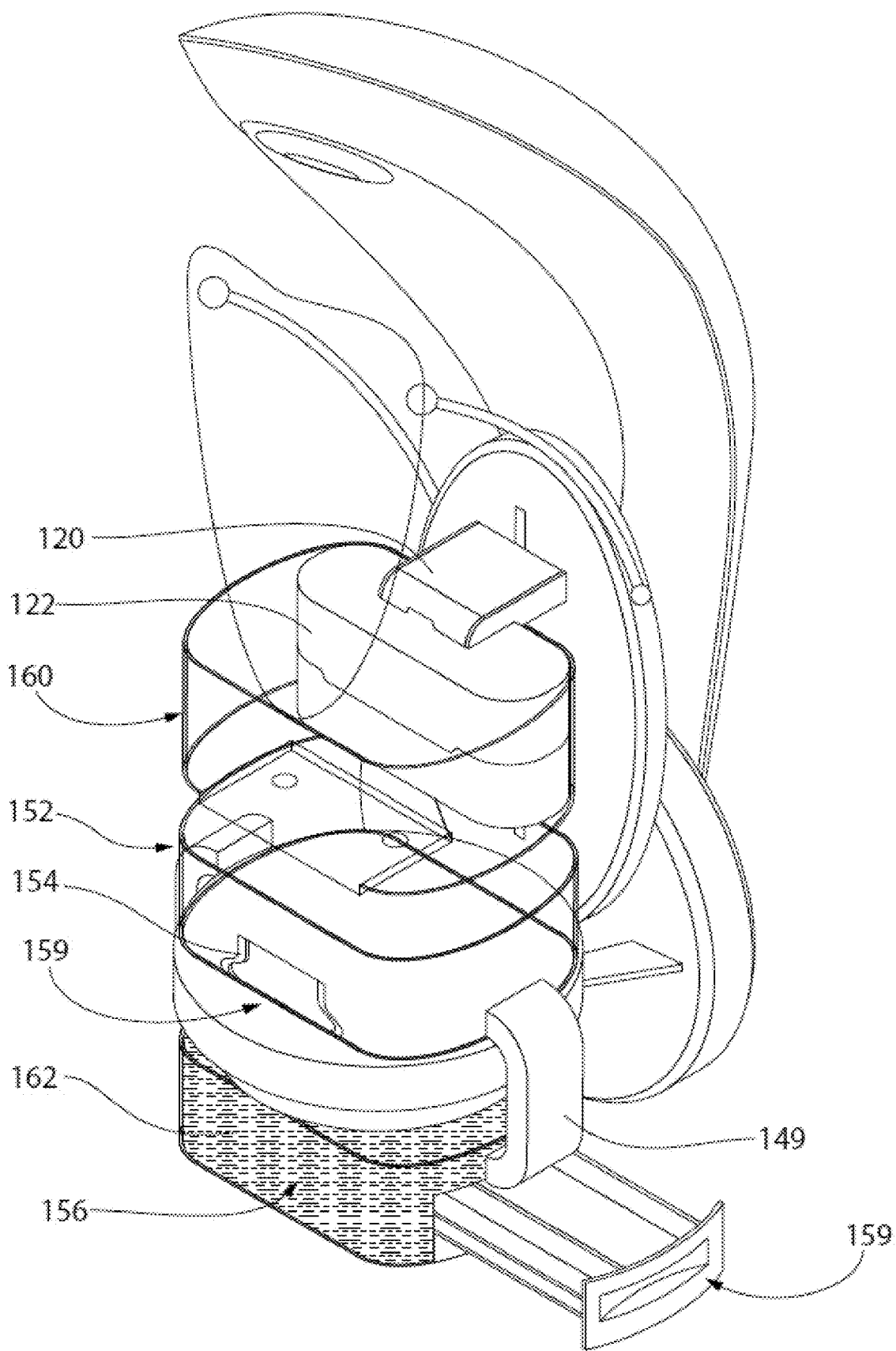
FIG. 2B is a perspective view of the breast examination housing assembly attached to the system according to one embodiment.

With reference now to FIGS. 2A and 2B, a breast examination housing assembly 150 is shown according to one embodiment. The breast examination housing assembly 150 includes an examination box 152 and a fluid box 156 positioned beneath examination box 152. The examination box 152 has an internal cavity 153 and an opening 155 to the internal cavity 153. At least a portion of the opening 155 includes a sealing fluff connected to perimeter portions of the opening 155. The fluid box 156 has an internal cavity 157 and a volume adjustment tray 158 that slides in and out of the lower box cavity 157 to push fluid up to the examination box 152 via the conduit 149 A compression plate 160 is configured to fit within a top opening 151 of the examination box 152. The compression plate 160 includes a recess 147 that can have one or more openings 154 for docking the probe 122. The breast examination housing assembly 150 configured onto the system is shown specifically in FIG. 2B. The compression plate 160 connects to the 3D ultrasound probe housing 122 which is connected to the moving arm 120. The examination box 152 rests on top of the table, and a low x-ray attenuation nipple coupling gel pad is positioned between the compression plate 160 to complete contact between the ultrasound probe housing 122 and the patient's breast tissue. The coupling gel pad can be left in place for both mammogram and ultrasound scans. In a preferred embodiment, instead of (or in addition to) a pad, a liquid form of coupling is utilized, such as nonstick gel or another fluid. The liquid coupling is pumped through the conduit from the bottom reservoir to the breast holding examination box compartment. This can be done after x-ray imaging and before ultrasound imaging.

Figure 3A:
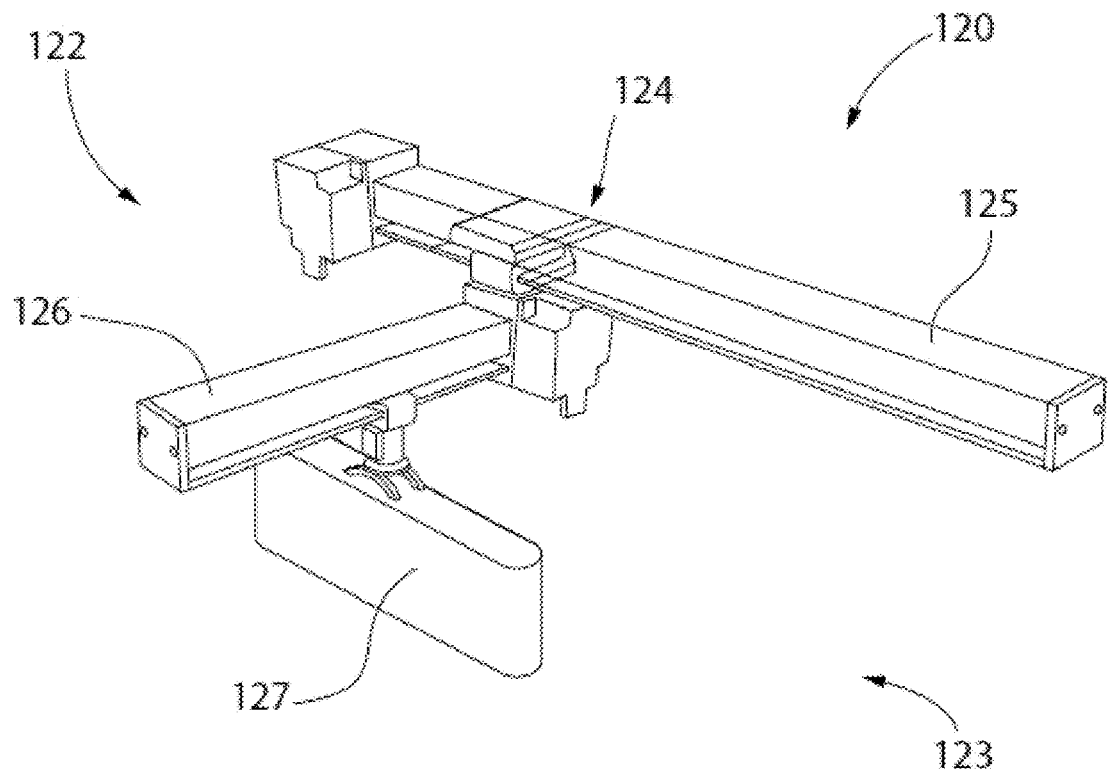
FIG. 3A is a perspective view of a 3D ultrasound probe attached to an extension rail and moving arm according to one embodiment.
Figure 3B:
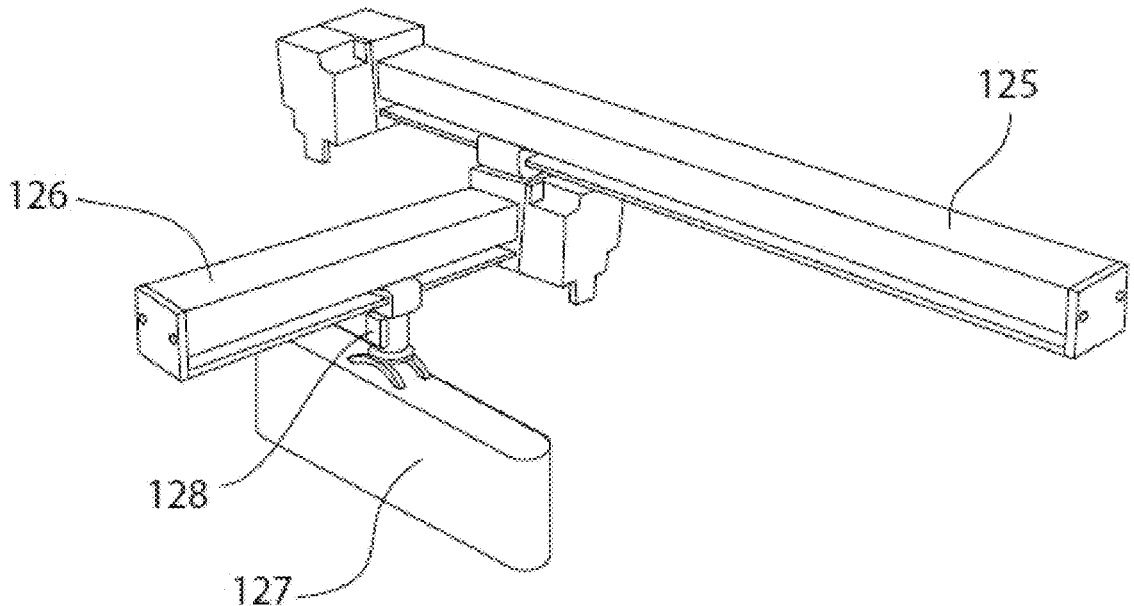
FIGS. 3B and 3C show slide rail assemblies of the probe according to one embodiment.
Figure 3C:
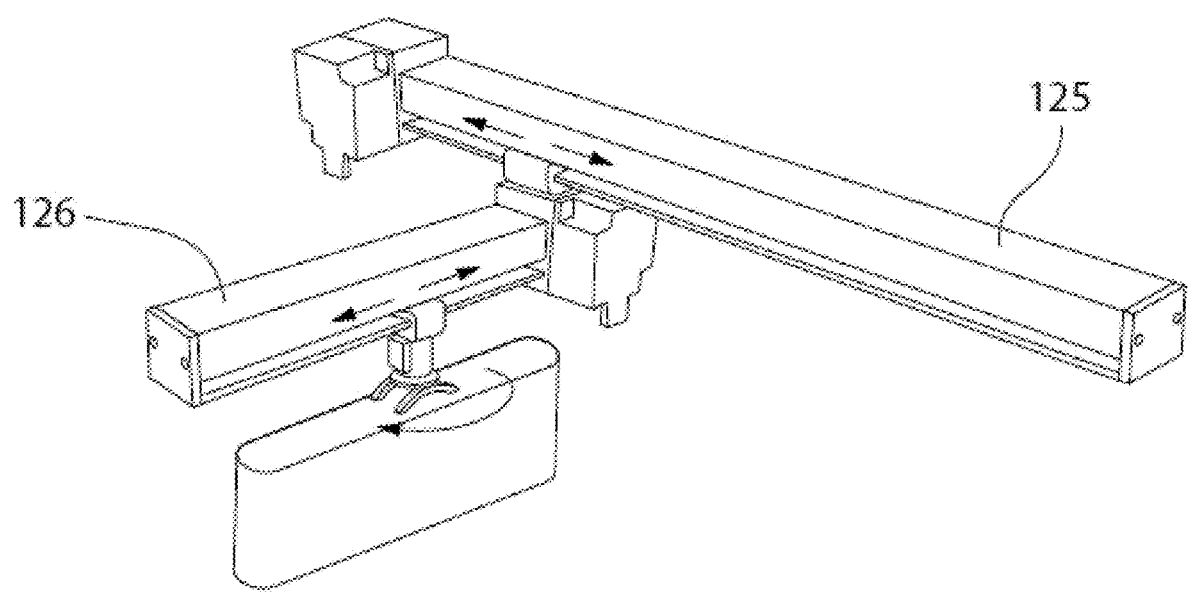

With reference now to FIGS. 3A-3C, components of the 3D ultrasound probe housing 123 are shown according to one embodiment. The moving arm 120 moves the probe housing 123 up and down along the height of the cabinet. The extension rail 124 moves the probe housing 123 towards and away from the moving arm 120. The slide rail (x) 125 and slide rail (y) 126 move the probe head 127 within the housing 123 along perpendicular axis. As shown specifically in FIG. 3C, the probe head 127 can also rotate about its motor connection 128 to the slide rail (y) 126.

Figure 4A:
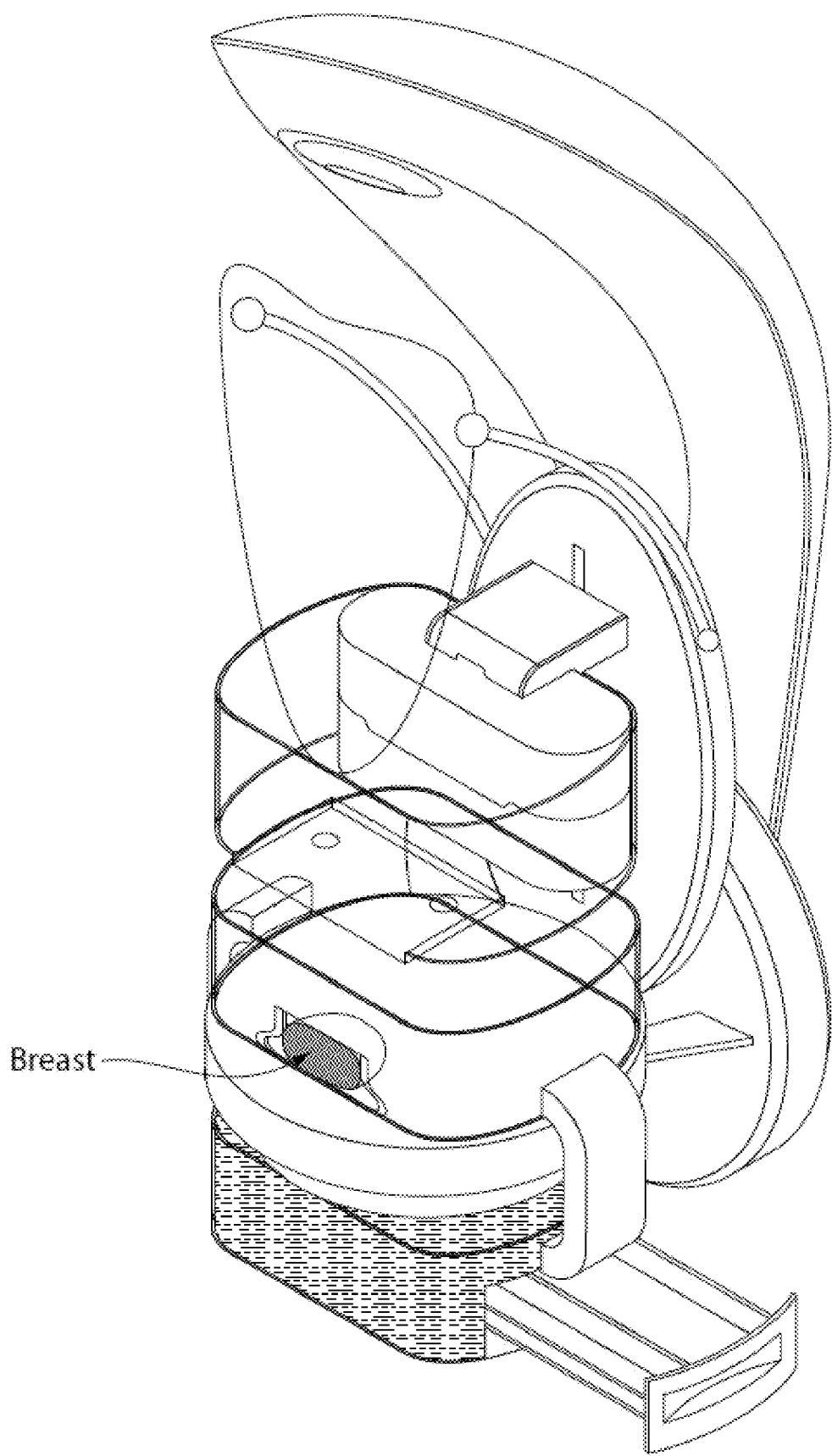
FIGS. 4A-4E illustrate steps of an examination procedure according to one embodiment.
Figure 4B:
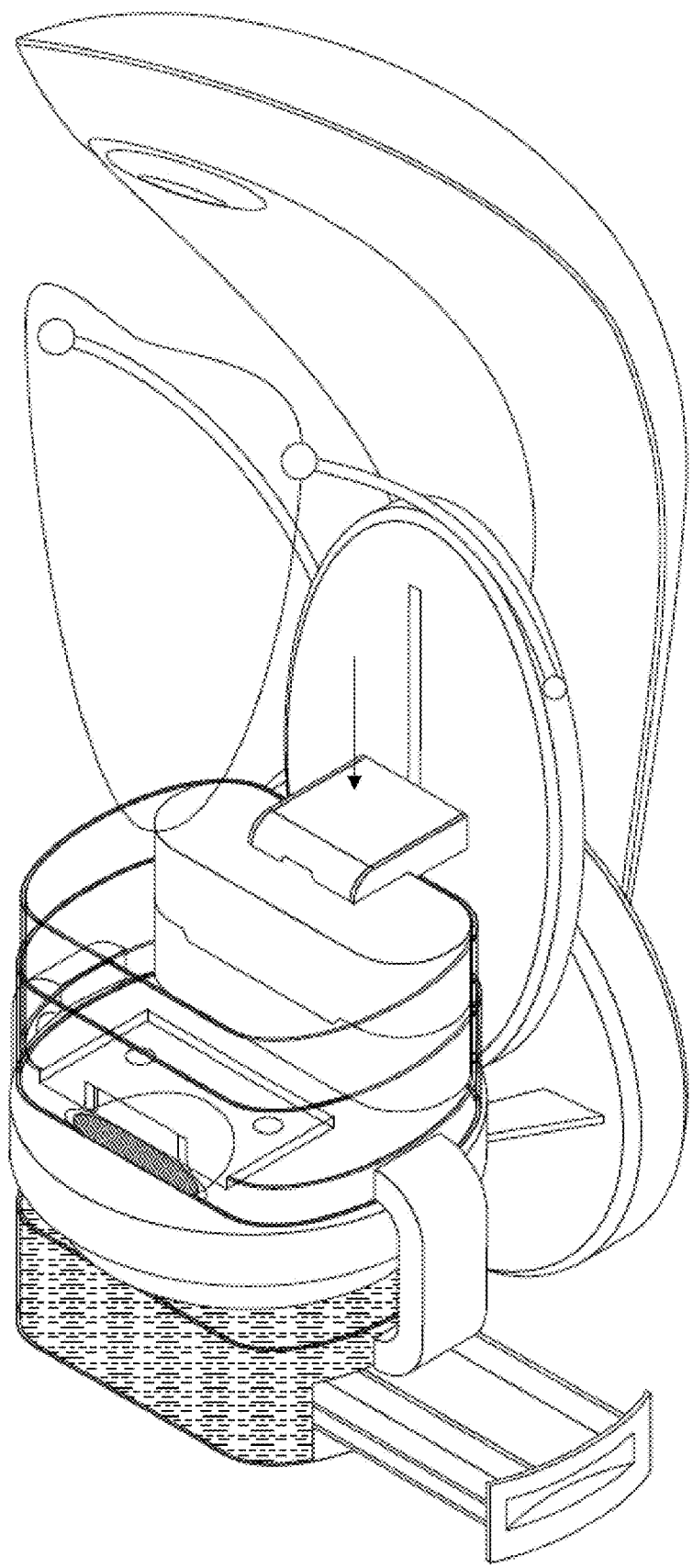
Figure 4C:
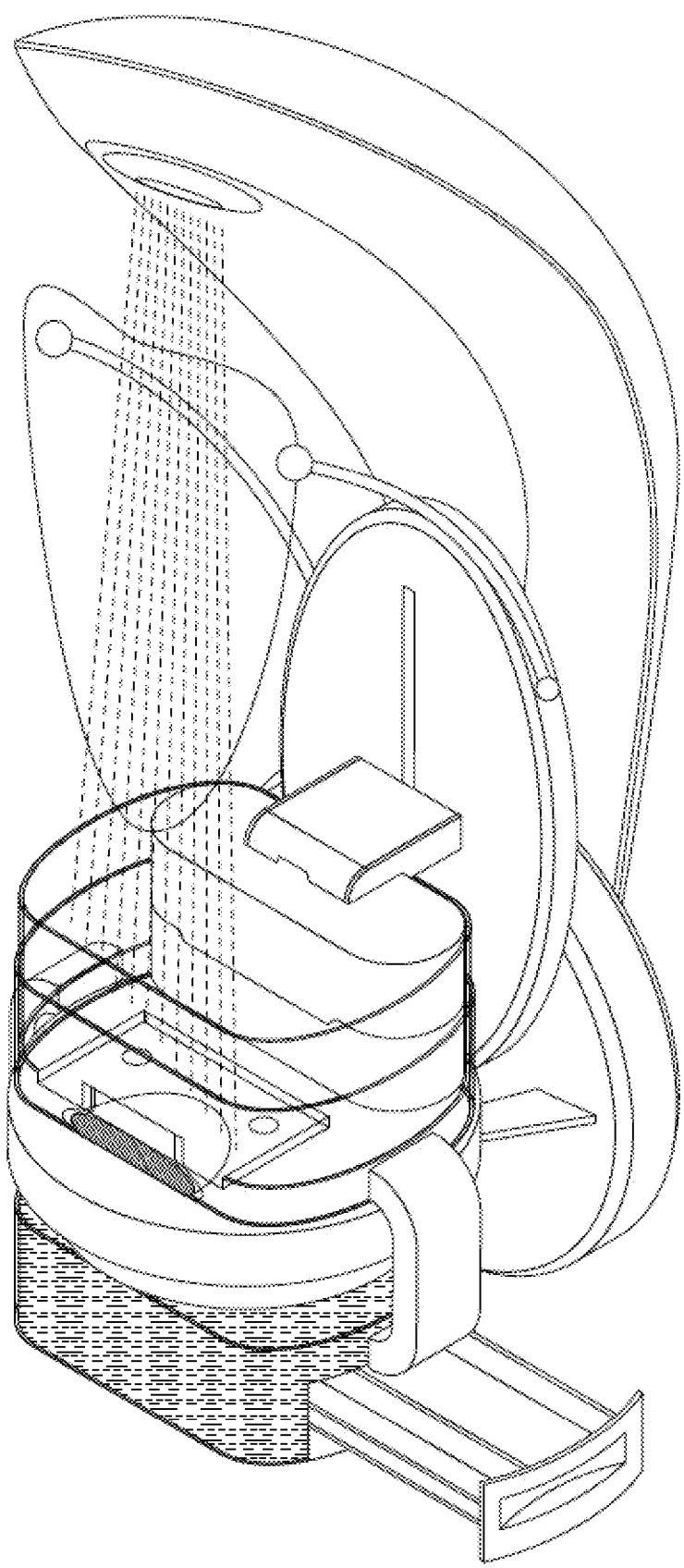
Figure 4D:
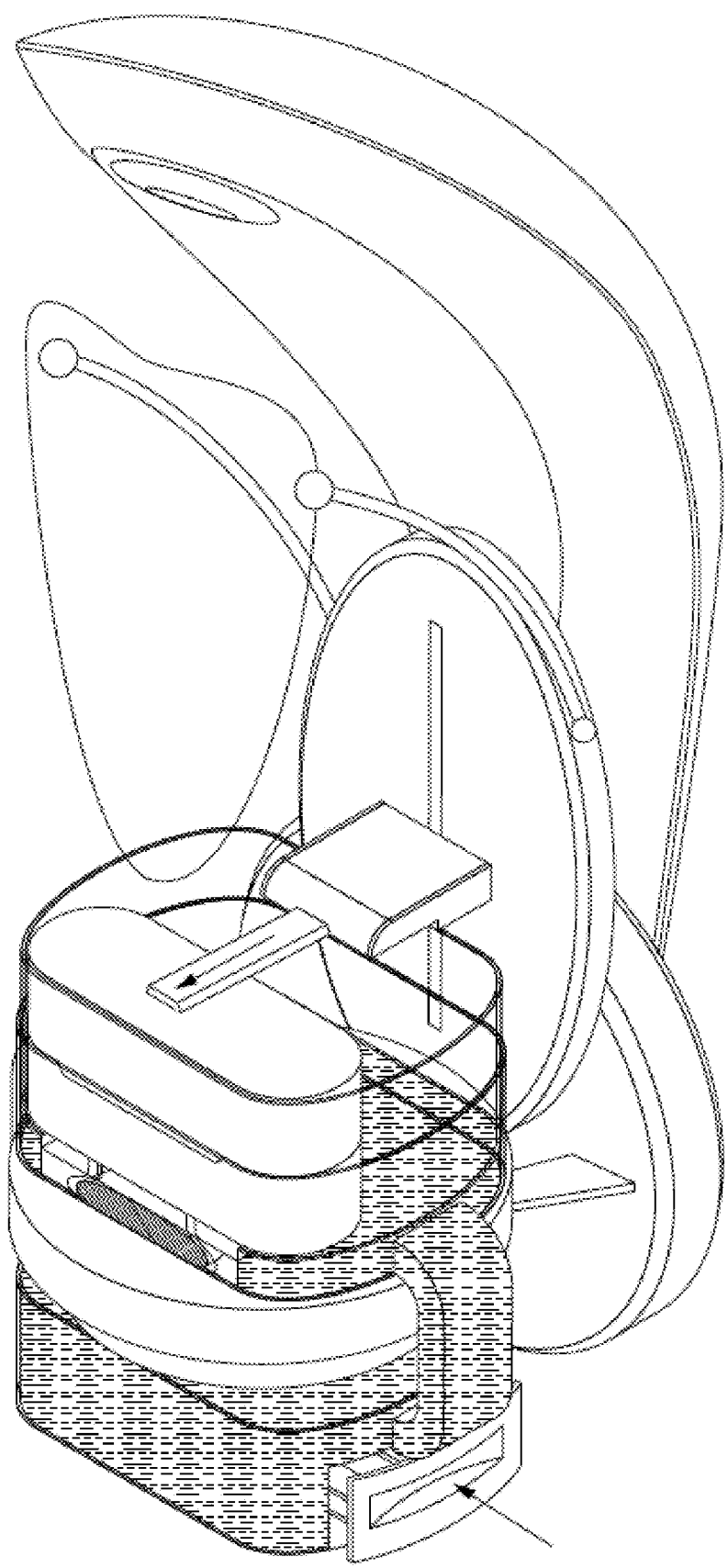
Figure 4E:
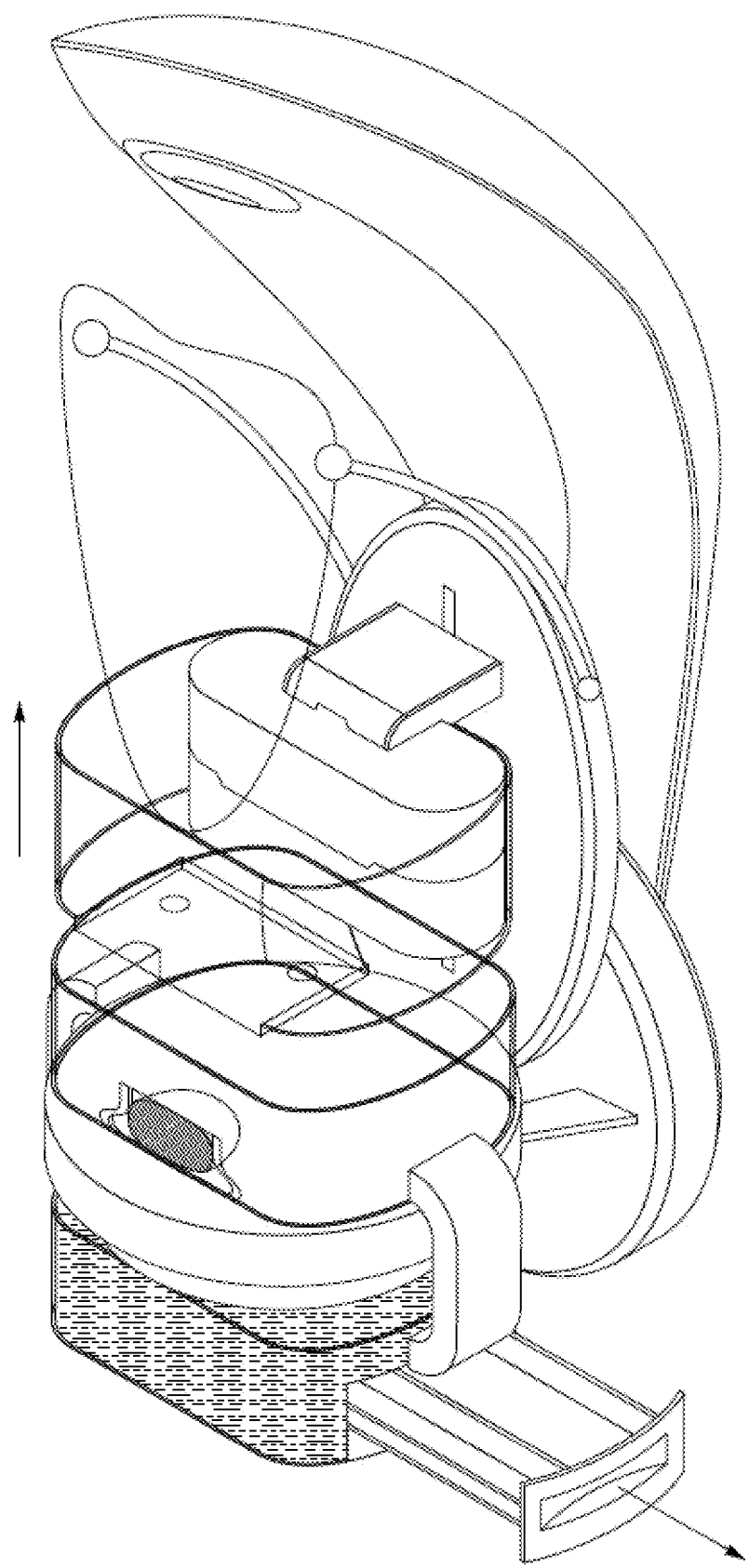

With reference now to FIGS. 4A-4E, a method of performing breast cancer detection procedure is shown according to one embodiment. First, the breast is inserted into the box opening (FIG. 4A). Next, the compression plate (connected to the ultrasound probe housing) is moved down into the box by actuating the moving arm in a downward direction (FIG. 4B). This movement clamps the breast and secures it from moving. Next, an x-ray inspection of the breast is performed (FIG. 4C). Next, the ultrasound inspection can begin (FIG. 4D). Pushing the volume adjustment tray into the box presses the non-stick fluid into the interspaces between the plate, box and the bottom of the probe. Moving the 3D probe forward along the extension rail docks the probe onto the compression plate and seals interspaces between the recess and bottom of probe. Next, the volume adjustment tray is pulled out and the plate is moved back up (FIG. 4E). The non-stick fluid flows back to the bottom of the box for the next inspection.

In one embodiment, the X-ray screen 130 and table 132 are moved out of the imaging area after X-ray mammography or digital breast tomosynthesis (DBT) is acquired, while the breast remains stationary in the examination box 152. The 3D ultrasound probe housing 123, which is mounted with the probe head 127 facing the breast being imaged is moved into the imaging area and in contact with the examination box. Ultrasound-compatible coupling gel may be applied as necessary to ensure acoustic contact between the ultrasound probe housing and the examination box. A sufficient layer of coupling fluid is introduced from the fluid box 156 via the conduit 149 to establish acoustic contact between the bottom of the examination box and the entire breast tissue. In this embodiment, it is not necessary to immerse the entire breast in the coupling fluid in order to image the whole breast by the ultrasound wave.

It is to be understood that the entire system 100 including the X-ray subsystem, the ultrasound subsystem and the breast immobilization subsystem can be used at any angle to the vertical, for example, in the so-called medio-lateral oblique direction, by rotating the imaging apparatus as a whole relative to the cabinet 140. A preferred embodiment includes a rotatable gantry on which the imaging and breast fixation subsystems are mounted. This gantry rotation is distinct from and independent of the possible rotation of the adjustable housing 101, the latter being a preferred embodiment of digital breast tomosynthesis (DBT) image acquisition.

Figure 5:
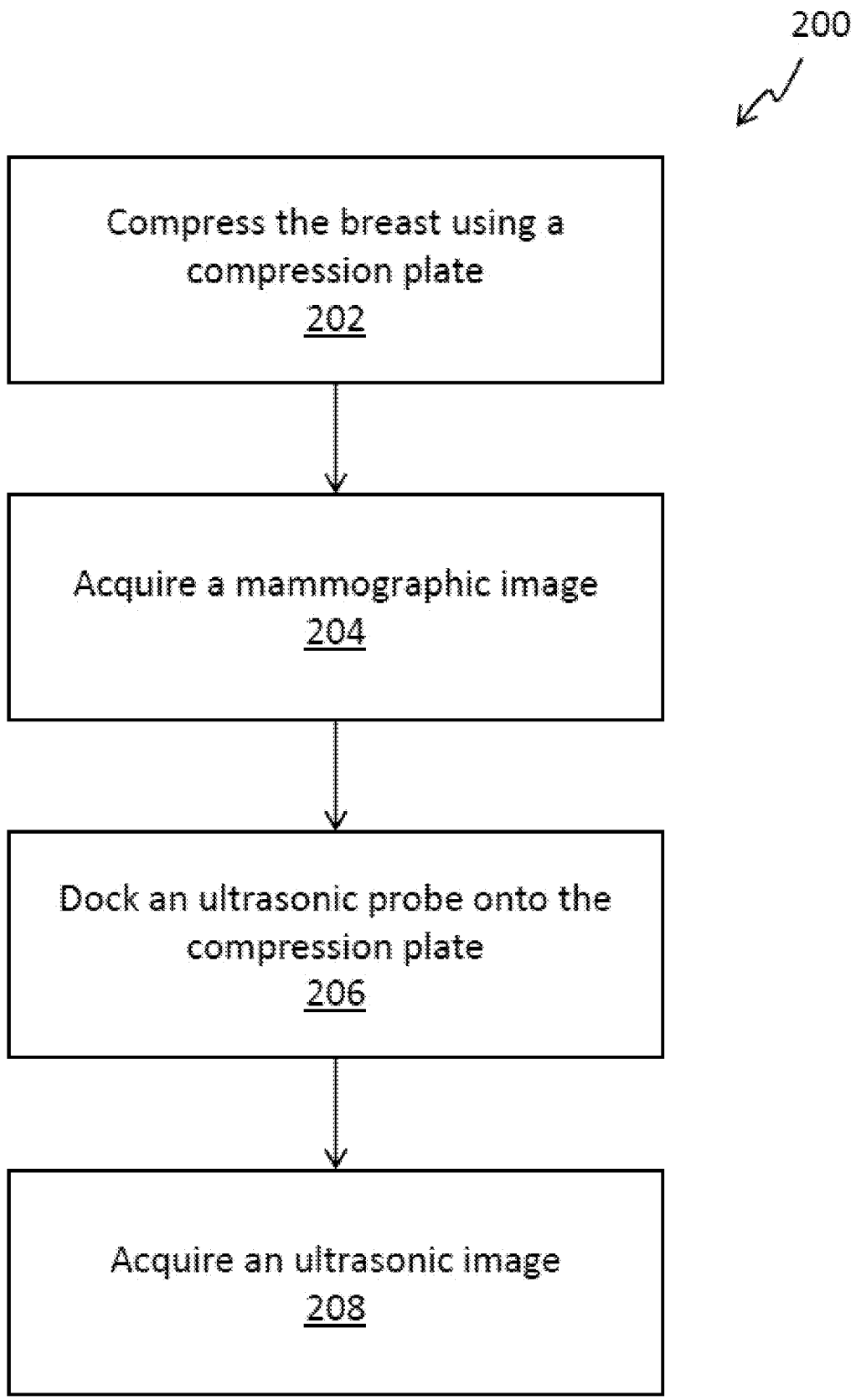
FIG. 5 is a flow chart of a method of performing a breast cancer detection procedure according to one embodiment.

With reference now to FIG. 5, a flow chart of a method 200 of acquiring co-registered images via co-localization of mammography and ultrasound for performing breast cancer detection is shown according to one embodiment. The method 200 includes the steps of compressing the breast using at least one compression plate 202, acquiring a mammographic image 204 while the subject remains in the same position, docking the ultrasonic scanner onto the compression plate 206, and acquiring at least one ultrasonic image 208. In one embodiment, the ultrasonic images are acquired while the ultrasound probe is scanned in one direction along the compressed breast. In one embodiment, the ultrasonic images are acquired while the ultrasound probe is scanned in two directions along the compressed breast. In one embodiment, the ultrasonic images are acquired while the ultrasound probe is rotated around the compressed breast. In one embodiment, the images acquired from scanning in the two different directions are compounded mathematically. In one embodiment, the narrow portions of the breast are padded by low X-ray attenuating acoustic contact material. In one embodiment, the narrow portions of the breast are filled in by fluid after X-ray and before ultrasound without altering the breast position. In one embodiment, the ultrasonic images are reduced to a planar image by raytracing along the mammographic X-ray direction and applying at least one image processing filter to the ultrasound image pixels. In one embodiment, the image processing filter simulates mammographic X-ray attenuation and transmission through the ultrasound images of the breast. In one embodiment, a computer interface permits the user to identify one region of interest in one image modality and the same region is identified and displayed in the other image modality.

Figure 6:
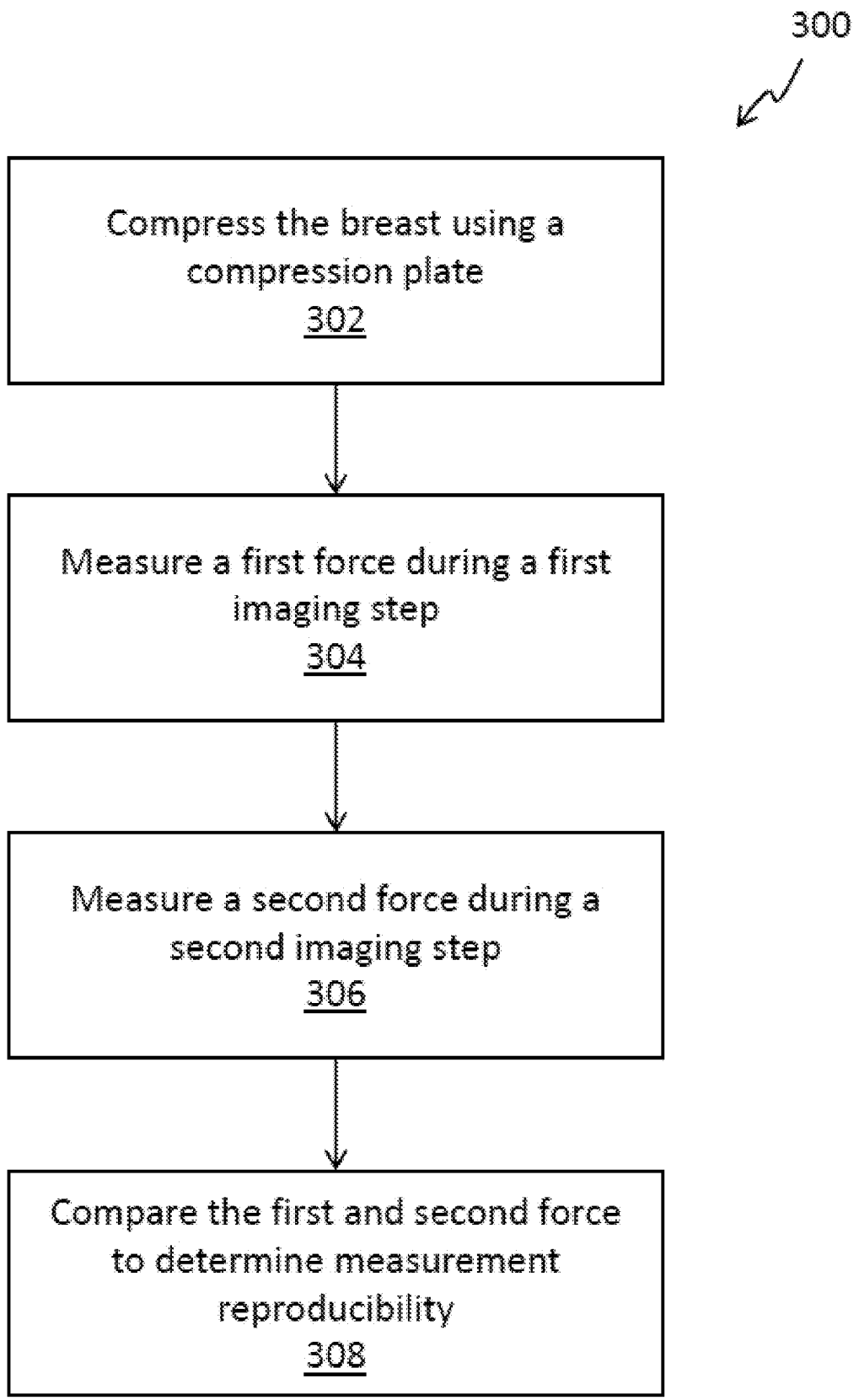
FIG. 6 is a flow chart of a method of imaging a breast according to one embodiment.

With reference now to FIG. 6, a method 300 of breast imaging includes the steps of compressing the breast, measuring a first force exerted in compressing the breast during a first imaging step, compressing the breast again at a later time, measuring a second force exerted in compressing the breast during a second imaging step, and comparing the first and second force to ensure reproducibility of the degree of compression. Determining reproducibility of the degree of breast compression between successive examinations (such as across different annual screening exams) can determine the ability to achieve the same or comparable images. In one embodiment, the compression force is reproduced as precisely as possible in successive imaging sessions. In one embodiment, images from successive sessions are compared by mathematical image processing, including co-registration, histogram equalization and subtraction.

Embodiments of the systems and methods described herein can implement various algorithms to process data and provide a diagnostic output. In one embodiment a method of discriminating anomalies in breast tissue from at least two different imaging modalities includes co-registering the imaging modalities, where the combined image data are processed by mathematical algorithms (e.g. machine learning, AI, etc.). In one embodiment, the co-registration is achieved by co-localizing the two different imaging modalities in the same exam. In one embodiment, the co-registration is achieved by reproducing the force exerted to the breast. In one embodiment, when acquiring ultrasound images of the breast, the breast is compressed along the direction of the ultrasound beam. In one embodiment, a high frequency ultrasound probe is used to achieve superior image resolutions.

Embodiments of the invention provide precise mammogram and 3D ultrasound co-registration by co-localized sequential/concurrent imaging, enabling the following unique features:

In one embodiment, the ultrasound scanning mechanism inside the scanner enclosure can scan along a single direction to acquire a single 3D image stack, or along two orthogonal directions to acquire two distinct 3D image stacks. In another embodiment, the two image stacks are fused together to form a third, "compounded" ultrasound 3D image stack.

Because the breast is compressed, ultrasound needs to penetrate shallower depths to image the entire breast. Consequently, higher resolution (e.g., high frequency ultrasound) imaging can be achieved compared to conventional ultrasound imaging. This aspect of the invention is referred to herein as "compressed ultrasound". By reducing the imaging depth due to compression, a higher frequency ultrasound can be utilized, which has higher spatial resolution and better imaging quality. In one embodiment, compressed ultrasound is performed within the high frequency range of 10 Mhz-30 Mhz, which is otherwise not suitable for accurately performing ultrasound examination on a typical uncompressed breast.

At least one image processing kernel can be applied through at least one of the above-mentioned compressed 3D ultrasound image stacks to generate a pseudo-transmission planar image in the same direction as the mammographic image. This aspect of the invention is referred to as "sono-mammography". The sono-mammogram so produced by applying any one of a number of pseudo-transmission kernels is precisely co-registered with the true mammogram, and thus can be displayed side by side, or in direct overlay fashion with optional checkerboard, cut-away or color wash toggles, or be subtract from each other to form a subtraction image.

Graphical user interfaces can be employed to take advantage of the co-registered multi-modality image sets as follows:

A user selects a mammogram region-of-interest (ROI) point, and the ultrasound display automatically moves to the scan plane or orthogonal scan plans that contain the ROI point.

A user draws an ROI line on mammogram, and the ultrasound display automatically reconstructs the plane containing the ROI line along the X-ray direction. The reconstructed image can be based on the single 3D ultrasound image stack, or the two orthogonal 3D ultrasound image stacks, or the compounded ultrasound 3D image stack.

A user selects an ultrasound ROI point, and the mammogram panel automatically shows the corresponding location on projection view and displays suitably magnified mammographic ROI in the corresponding area.

Co-registered mammogram, 3D compressed ultrasound and its various sono-mammograms contain highly correlated but mutually complementary information about breast tissue anomalies, morphological and textual features, which are amenable to artificial intelligence classification via machine learning. Embodiments of the invention utilize co-localization of the multimodality image data, which makes cross-referencing the image feature spaces possible and precise. An example embodiment of this aspect of the invention is to treat the mammogram, sono-mammograms and compressed ultrasound stacks as feature maps in a "deep learning" convolution neural network (CNN). The CNN can be trained by prior example cases of histology confirmed true positive, false positive, true negative and false negative feature maps. The fully trained CNN will then serve as an automated breast cancer classifier of the combined mammogram-ultrasound image set. In another embodiment, the same histology confirmed ground truth data and image feature maps can be used in combination to derive the most diagnostically accurate pseudo-transmission kernel for reducing a 3D compressed ultrasound image stack to a sono-mammogram.

Another novel aspect of the embodiments described herein relate to methods to achieve greater consistency and reproducibility of the breast compression. The utility of this approach is to permit more accurate longitudinal comparison of images of the breast either by human observer or by computer algorithms. Currently, breast compression is performed without quantitative accuracy, and therefore the resulting images of the breast from one exam to the next cannot be rigorously co-registered. Expert observers (e.g. radiologists) must mentally register images in order to perform longitudinal comparison. Longitudinal comparison is a hallmark of breast cancer screening and detection. According to embodiments of the present invention, at least one force sensor is attached to the compression plate. The amount of compression force is established at a baseline exam, and is thereafter matched as precisely as possible in follow-up exams. In the case of unavoidable drift of the baseline (e.g. due to breast size change), a new baseline compression force can be established when necessary. The resulting images from successive exams can be co-registered subjectively or mathematically, and in the latter case, subtraction and other image manipulation algorithms can be applied to enhance significant changes in the breast.

Another novel aspect of the embodiments described herein relate to methods to acquire only a single set of X-ray mammography or digital breast tomography from one view of a breast. If breast compression is to be used, the breast is only compressed in one direction. Ionizing X-ray radiation dose is reduced by half compared to current state of the art. Embodiments of the invention include the option of shaping the X-ray imaging screen and supporting table to allow a patient to step into the X-ray field and to position the patient's breast tissue more completely on the imaging screen. In one embodiment, the X-ray field can be collimated to the breast shape using adjustable multiple leaf segments made of suitably attenuating material such as tungsten. Embodiments of the invention also permit mild compression or no compression when digital breast tomography images are acquired. According to embodiments of the present invention, X-ray image set from this one view is co-registered with 3D ultrasound of the same view. In one embodiment, no compression or mild compression digital breast tomography is implemented. In one embodiment, a concavely shaped X-ray imaging screen and supporting table are utilized to accommodate the patient's habitus and capture entire breast tissues in the image field. In one embodiment, a multi-leaf collimator is implemented to shape the X-ray field when a patient's habitus is otherwise exposed in the field. Thus, embodiments of the system may include an x-ray device configured to generate at least one mammography image, and a concavely shaped X-ray imaging screen and supporting table configured to accommodate the patient's habitus and capture all breast tissues in the image field for generating the at least one mammography image. Accordingly, embodiments may also include a system for breast imaging includes an x-ray device configured to generate at least one mammography image, and a multi-leaf collimator configured to shape the X-ray field when a patient's habitus is otherwise exposed in the field for generating the at least one mammography image. In embodiment, imaging is conducted in one view only and digital breast tomography is co-registered with 3D ultrasound.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A system for breast cancer detection using co-localized ultrasound mammography comprising:
    an examination box comprising a side wall surrounding a cavity and forming a perimeter of a top opening, wherein the side wall comprises a side opening connected to the cavity, and wherein at least a portion of the side wall extends above the side opening to the perimeter;
    a compression plate connected to an actuator, the actuator configured to advance a surface of the compression plate towards a breast adapted to be positioned within the cavity from the side opening to compress and stabilize the breast;
    an x-ray device configured to generate at least one mammography image;
    an ultrasound probe configured to generate at least one ultrasound image; and
    a controller operably connected to the x-ray device and the ultrasound probe, the controller configured to generate a colocalized image based on co-localization of the at least one mammography image and at the least one ultrasound image.

2. The system of claim 1 further comprising:
    a fluid box in fluid communication with the examination box via a conduit.

3. The system of claim 2 further comprising:
    a slidable volume adjustment tray configured into an opening of the fluid box.

4. The system of claim 1, wherein the compression plate comprises an interior recess configured to dock the ultrasound probe without an air gap.

5. The system of claim 1, wherein the side opening comprises a resilient sealing material configured around at least a portion of a perimeter of the side opening.

6. The system of claim 1, wherein the actuator is a mechanical arm.

7. The system of claim 1, wherein the ultrasound probe further comprises a probe head disposed within a housing.

8. The system of claim 7, wherein the probe head is connected to a dual rail system comprising a first axis rail connected perpendicularly to a second axis rail.

9. The system of claim 8, wherein the probe head is connected to at least one of the first axis rail and the second axis rail by a rotatable connector.

10. The system of claim 1, wherein the compression plate is positioned above the examination box and the actuator is configured to advance the compression plate downwards into the cavity for compressing and stabilizing the breast during examination.

11. The system of claim 10, wherein a fluid box is positioned below the examination box.

12. The system of claim 10, wherein the ultrasound probe is positioned above the examination box.

13. The system of claim 10, wherein the x-ray device is positioned above the ultrasound probe.

14. The system of claim 1, wherein the compression plate is positioned below the examination box and the actuator is configured to advance the compression plate upwards into the cavity for compressing and stabilizing the breast during examination.

15. The system of claim 1 further comprising:
    a baffle positioned adjacent to the x-ray device.

16. The system of claim 1, wherein the compression plate comprises a low x-ray attenuation material.

17. The system of claim 1 further comprising:
    a low x-ray attenuation coupling gel pad for placement within the cavity during an examination.

18. The system of claim 1, wherein the ultrasound probe is configured to generate the at least one ultrasound image at a frequency ranging 10 Mhz-30 Mhz.

19. The system of claim 1, wherein the at least one mammography image is an at least one 3D tomographic mammography image, the at least one ultrasound image is an at least one 3D ultrasound image, and the controller is configured to generate the colocalized image based on co-localization of the at least one 3D tomographic mammography image and the at least one 3D ultrasound image.

* * * * *